US011801370B2

(12) United States Patent
Anderson, Jr.

(10) Patent No.: US 11,801,370 B2
(45) Date of Patent: Oct. 31, 2023

(54) GAS MANAGEMENT FOR JETTING CARTRIDGE

(71) Applicant: Funai Electric Co., Ltd., Osaka (JP)

(72) Inventor: James D. Anderson, Jr., Lexington, KY (US)

(73) Assignee: Funai Electric Co., Ltd.

( * ) Notice: Subject to any disclaimer, the term of this patent is extended or adjusted under 35 U.S.C. 154(b) by 384 days.

(21) Appl. No.: 17/248,996

(22) Filed: Feb. 17, 2021

(65) Prior Publication Data

US 2022/0257914 A1 Aug. 18, 2022

(51) Int. Cl.
*A61M 31/00* (2006.01)
*A61M 5/30* (2006.01)

(52) U.S. Cl.
CPC .............. *A61M 31/00* (2013.01); *A61M 5/30* (2013.01); *A61M 2205/75* (2013.01); *A61M 2210/0618* (2013.01)

(58) Field of Classification Search
CPC .... A61M 31/00; A61M 5/30; A61M 2205/75; A61M 2210/0618; A61M 5/00; A61M 15/025; A61M 15/08; B41J 2/14145; B41J 2/17513; B41J 2/19; B41J 2/175
See application file for complete search history.

(56) References Cited

U.S. PATENT DOCUMENTS

| | | | |
|---|---|---|---|
| 639,601 A | 12/1899 | Mcallister et al. | |
| 5,619,239 A | 4/1997 | Kotaki et al. | |
| 6,193,356 B1 | 2/2001 | Takata | |
| 6,402,311 B1 | 6/2002 | Inoue et al. | |
| 6,517,511 B2 * | 2/2003 | Yao | A61M 1/772 606/162 |
| 6,543,876 B2 | 4/2003 | Kotaki | |
| 9,987,644 B1 | 6/2018 | Anderson, Jr. | |
| 10,688,793 B1 | 6/2020 | Anderson, Jr. et al. | |
| 2001/0048457 A1 | 12/2001 | Hara et al. | |
| 2004/0189761 A1 * | 9/2004 | Amma | B41J 2/17513 347/93 |
| 2004/0239737 A1 | 12/2004 | Hara et al. | |
| 2004/0263591 A1 | 12/2004 | Hara et al. | |
| 2005/0062814 A1 | 3/2005 | Yildirim et al. | |
| 2019/0009568 A1 | 1/2019 | Koyano et al. | |

FOREIGN PATENT DOCUMENTS

JP 2008238783 A 10/2008

* cited by examiner

*Primary Examiner* — Nathan R Price
*Assistant Examiner* — Fatimata Sahra Diop
(74) *Attorney, Agent, or Firm* — Luedeka Neely, P.C.

(57) ABSTRACT

A cartridge having a reservoir for fluid, a tower with an interior chamber, wherein the tower has a first end proximate the reservoir, a second end distal the reservoir, a port in the second end of the tower, and an interior for conducing the fluid from the reservoir. A first rib and a second rib extend along a length of the tower, in the interior of the tower. Both the first and second ribs have second ends that are substantially adjacent the second end of the tower, and the first rib has a first end that extends along the length of the tower toward the first end of the tower further than a first end of the second rib. At least one of the first and second ribs at least partially overlaps a first via within the port and is spaced apart from the first via by a gap.

20 Claims, 4 Drawing Sheets

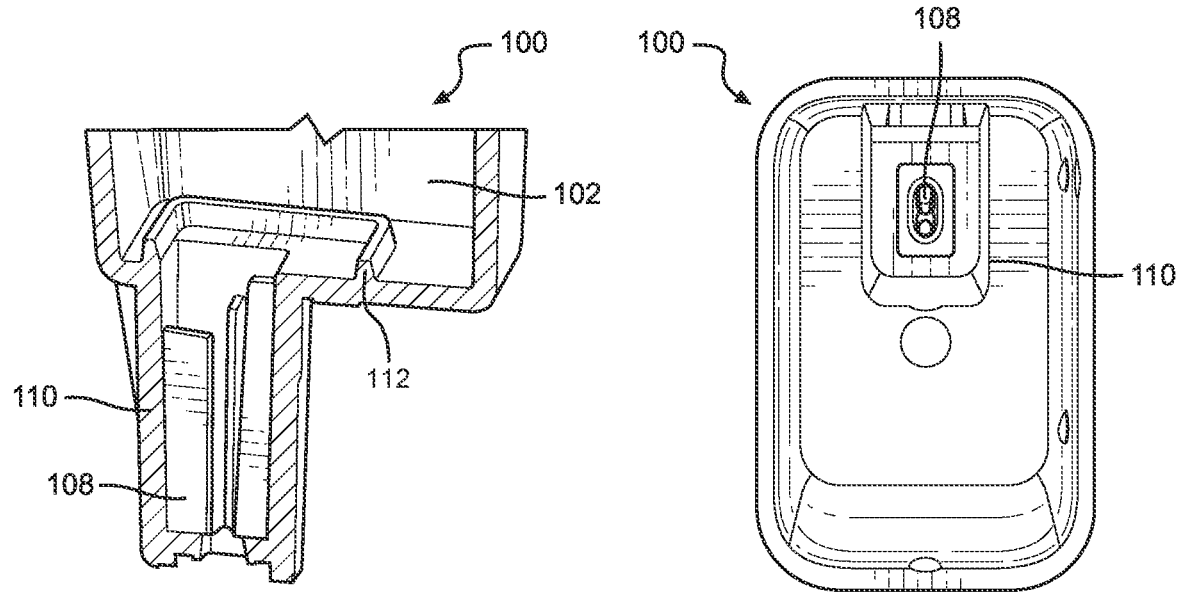
FIG. 5           FIG. 6
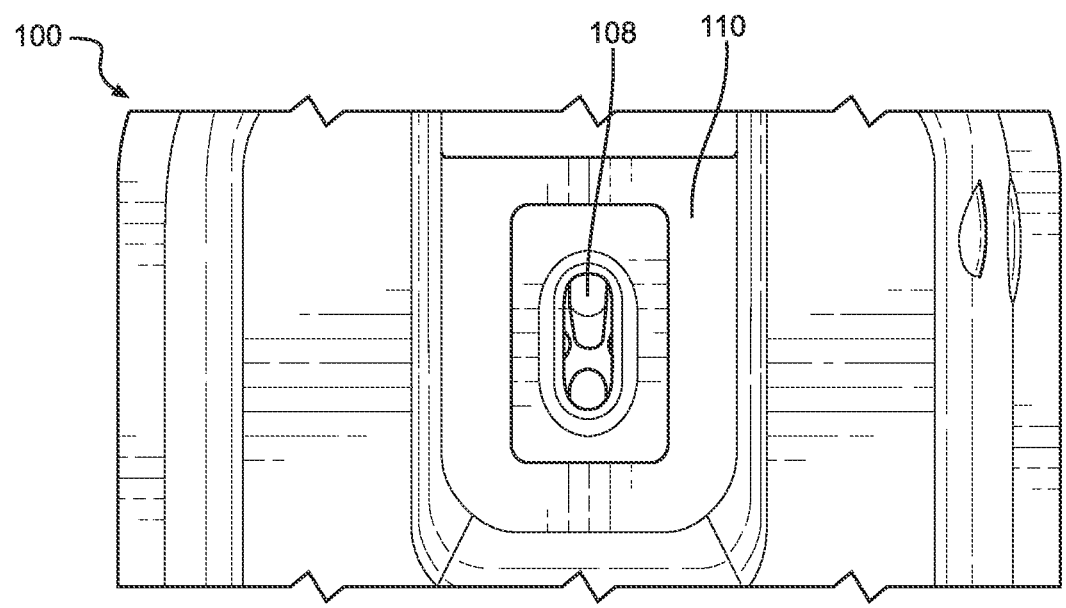
FIG. 7

GAS MANAGEMENT FOR JETTING CARTRIDGE

FIELD

This invention relates to the field of fluid jetting cartridges. More particularly, this invention relates to the management of gas bubbles within fluid jetting cartridges.

INTRODUCTION

Fluid jetting technology is similar to inkjet technology, but is used to express fluids other than inks. For example, a fluid jet cartridge could express various combinations of one or fluid medications, which could be delivered in a variety of different ways, such as via oral or nasal passages or tissues.

Fluid jetting technology uses, among other things, a cartridge that in its basic form is comprised of a reservoir and a jetting head. The reservoir holds the liquid to be expelled by the cartridge, which can be ink, but can also be other fluids. A given cartridge might have only a single reservoir with a single fluid to be ejected. However, another cartridge might have several reservoirs containing several different fluids to be ejected.

Regardless of the fluid to be expressed, it is possible for gas, such as air, to be entrained within the fluid reservoir in the cartridge. In most situations in which the cartridge is used, the jetting head is either below or horizontally adjacent the cartridge, and so any air or other gas that is entrained in the fluid does not naturally flow to the junction between the reservoir and the jetting head.

However, some situations require a jetting cartridge to express the fluid in a substantially vertically-upward direction, such as to a nasal cavity. In this configuration, any gas that is within the fluid reservoir of the cartridge will naturally flow up toward the jetting head. This condition tends to impede the fluid from flowing out of the reservoir and into the jetting head, thus rendering the cartridge inoperable.

What is needed, therefore, is something that tends to reduce issues such as those described above, at least in part.

SUMMARY

The above and other needs are met by a cartridge for jetting a fluid. A reservoir holds and provides the fluid. A tower with an interior chamber receives the fluid from the reservoir and provides the fluid. The tower has a first end proximate the reservoir, a second end distal the reservoir, a port in the second end of the tower, and an interior for conducting the fluid from the reservoir. A first rib and a second rib extend along a length of the tower between the first and second ends of the tower, in the interior of the tower. Both the first rib and the second rib have second ends that are substantially adjacent the second end, and the first rib has a first end that extends along the length of the tower toward the first end of the tower further than a first end of the second rib. A jetting head has a first via for receiving the fluid from the port and expressing the fluid from the cartridge. At least one of the first rib and the second rib at least partially overlaps the first via within the port and is spaced apart from the first via by a gap.

In various embodiments according to this aspect of the invention, the second ends of the first and second ribs are not parallel to a receiving surface of the jetting head in which the via is formed. In some embodiments, the tower includes a third rib that extends to a different distance than either the first rib or the second rib along the length of the tower. In some embodiments, the gap is from about three hundred microns to about five hundred microns. In some embodiments, the jetting head includes a second via, and the first rib at least partially overlaps the first via and the second rib at least partially overlaps the second via. In some embodiments, the cartridge is a nasal drug delivery cartridge. In some embodiments, the ribs tend to prohibit gas bubbles from aspirating into the via when the cartridge is oriented with the tower above the reservoir. In some embodiments, the via and the second ends of both the first and second ribs are and oriented substantially parallel one to another. In some embodiments, the via and the second ends of both the first and second ribs are and the second ends of the first and second ribs are oriented substantially perpendicularly one to another.

DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 5 is a partial side perspective cross-sectional view of a cartridge in a downward orientation according to a first embodiment of the present invention.

FIG. 6 is a bottom plan view of the exterior of a cartridge according to a first embodiment of the present invention.

FIG. 7 is an enlarged partial bottom plan view of the exterior of a cartridge according to a first embodiment of the present invention.

DESCRIPTION

Figure 1:
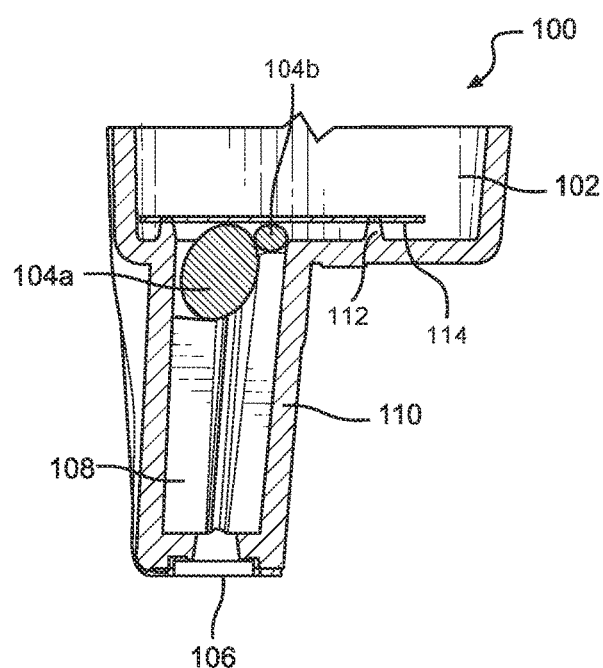
FIG. 1 is a partial side cross-sectional view of a cartridge in a downward orientation according to a first embodiment of the present invention.

With reference now to FIG. 1, there is depicted a partial side cross-sectional view of a cartridge 100 in a downward orientation, such as a maintenance orientation, according to a first embodiment of the present invention. The cartridge 100 comprises the reservoir 102, a tower 110, and a jetting head 106. Additional descriptions in regard to each of these basic elements of the cartridge 100 are provided below.

The reservoir 102 contains one or more chambers with one or more fluids to be expressed by the jetting head 106. Although the embodiments of the present invention are applicable to cartridges 100 that express more than one fluid, the embodiments described herein express only a single fluid, so to not unnecessarily encumber the drawings. But it is understood that a greater number of fluids is contemplated.

The tower 110 conducts the fluid to be expressed from the reservoir 102 to the jetting head 106 through a filter 114 that is attached to the reservoir 102 with an attachment surface 112. The tower 110 is that portion of the cartridge 100 between the filter 114 and the jetting head 106. As can be seen in FIG. 1, there may be one or more gas bubbles 104a and 104b entrained in the fluid. When the cartridge 100 is disposed with the tower 110 in downward orientation, the gas bubbles 104a and 104b tend to stay near the end of the tower 110 that is proximate the reservoir 102 and filter 114. When the gas bubbles 104a and 104b are in this position, they do not pose much of a problem to the proper flow of the fluid from the reservoir 102 to the jetting head 106.

Figure 2:
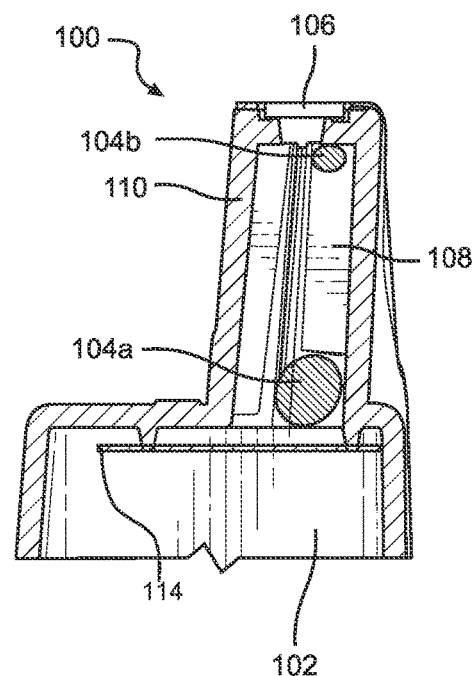
FIG. 2 is a partial side cross-sectional view of a cartridge in an upward orientation according to a first embodiment of the present invention.

However, when the cartridge 100 is inverted, as depicted in FIG. 2, with the tower 110 in an upward orientation, such as in a delivery orientation, the bubbles 104a and 104b tend to migrate near the end of the tower 110 that is distal the reservoir 102 and filter 114. As can be seen in FIG. 2, the smaller gas bubble 104b has moved to the distal end, but to a position in which it does not interfere to a destructive degree with the flow of the fluid to the jetting head 106. The larger gas bubble 104a has not moved to the distal end in the embodiment depicted in FIG. 2.

The reason that neither of the gas bubbles 104a and 104b have moved into a position in which they substantially impede the flow of the fluid from the reservoir 102 to the jetting head 106, is the presence of ribs 108 in the tower 110, which ribs 108 create flow channels within the tower 110. The ribs 108 are placed, in one embodiment, so as to create flow channels of various sizes between the ribs 108 and within the tower 110. Gas bubbles 104a and 104b tend to flow through whichever flow channel within the tower 110 that will accommodate the size of the particular gas bubble 104a and 104b, and then stay there, allowing the fluid to flow through other flow channels that were too small to pass the gas bubble 104a and 104b.

In various embodiment, the ribs 108 are placed at different angles with regard to the surface of the chip 106. In some embodiment, the ribs 108 are disposed at an angle of about five degrees from perpendicular with respect to the surface of the chip 106. In other embodiments they are disposed at a different angle, and in other embodiments they are substantially perpendicular to the surface of the chip 106.

So, as depicted in FIG. 2, the larger gas bubble 104a cannot move up through any of the flow channels between the ribs 108, but is trapped by the end of one of the ribs 108, while the fluid flows past the gas bubble 104a in the other flow channels. The smaller gas bubble 104b is small enough the flow completely up through one of the flow channels that is formed between the ribs 108, but then is trapped by its size within that flow channels by the proximity of the ribs 108, once again allowing the fluid to flow to the jetting head 106 through others of the flow channels between the ribs 108.

In this manner, by the placement of ribs 108 in the tower 110, flow channels are formed that tend to trap and retain gas bubbles 104a and 104b within them, thus preventing the gas bubbles 104a and 104b from attaining a position adjacent the jetting head 106 and cutting off the flow of the fluid to the jetting head 106. Different embodiments and views of the ribs 108 are described below, so as to provide a better comprehension of the embodiments of the invention.

Figure 3:
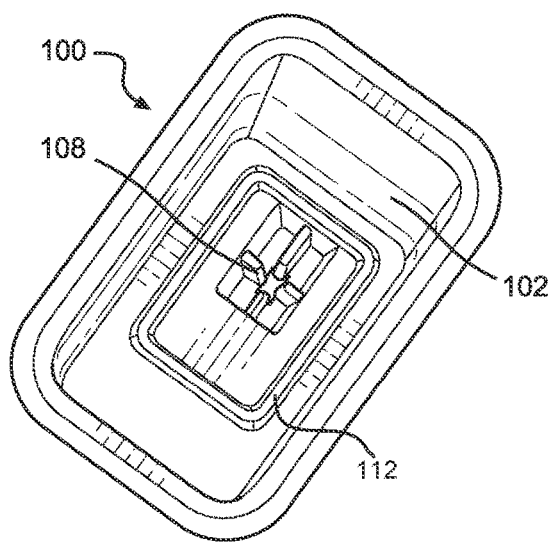
FIG. 3 is a top perspective view of the interior of a cartridge according to a first embodiment of the present invention.
Figure 4:
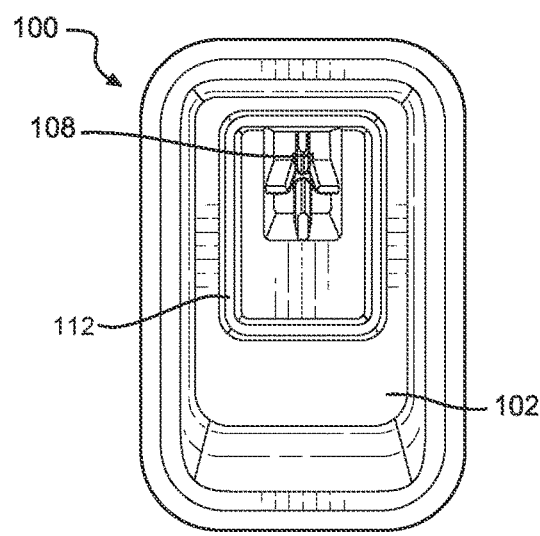
FIG. 4 is a top plan view of the interior of a cartridge according to a first embodiment of the present invention.

With reference now to FIG. 3, there is depicted a top perspective view of the interior of a cartridge 100 according to a first embodiment of the present invention. This view looks down through the reservoir 102 to see the ribs 108 in the tower 110. In this embodiment, the ribs 108 form the four arms of a cross within the tower 110, with a void in the middle of the cross, so that none of the four arms meet with one another. Thus, flow channels are formed in the spaces between all of the ribs 108. FIG. 4 provides another top view of the ribs 108.

With reference now to FIG. 5, there is depicted a partial side perspective cross-sectional view of a cartridge 100 in a downward orientation according to the first embodiment of the present invention. In this embodiment, the ribs 108 extend to different lengths from the distal end of the tower 110 toward the reservoir 102. These different lengths create partial flow channels at the ends of the ribs 108, which can accommodate larger gas bubbles 104a and 104b, while smaller gas bubbles 104a and 104b can travel through the flow channels formed between the ribs 108. Thus, in some embodiments, all of the ribs 108 have different lengths, and in other embodiments, all of the ribs 108 have the same length. In some embodiments the ribs 108 all extend to what can be termed the top or the proximate end of the tower 110, and in other embodiments the ribs 108 extend to different lengths, as depicted in FIG. 5.

With reference now to FIG. 6, there is depicted a bottom plan view of the exterior of a cartridge 100 according to the first embodiment of the present invention. In this view, the jetting head 106 is not attached, so as to show some of the detail of the ribs 108 that is visible through the fluid passage at the distal end of the tower 110. As can be seen, some of the ribs 108 block some of the fluid passage, but do not completely block it. FIG. 7 provides an enlarged portion of the same view as FIG. 6, where the ends of the ribs 108 can be more easily seen through the fluid passage in the tower 110.

Figure 8:
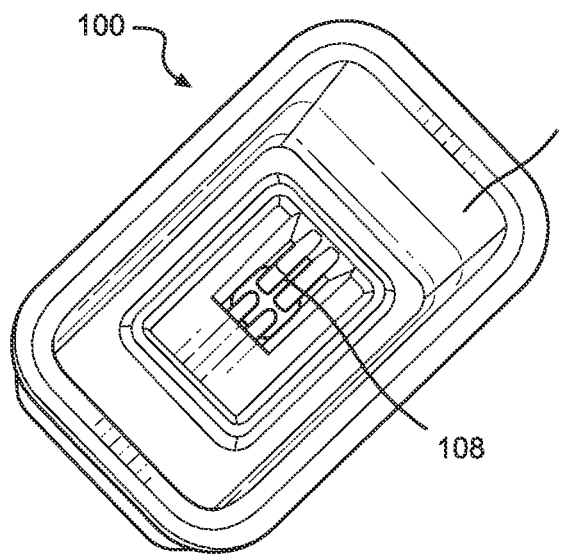
FIG. 8 is a top perspective view of the interior of a cartridge according to a second embodiment of the present invention.
Figure 9:
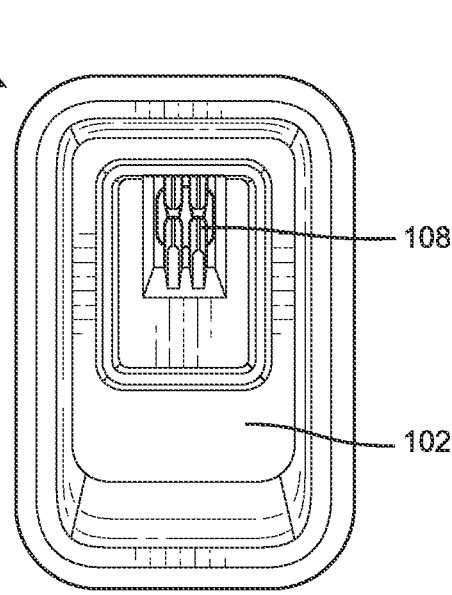
FIG. 9 is a top plan view of the interior of a cartridge according to a second embodiment of the present invention.
Figure 10:
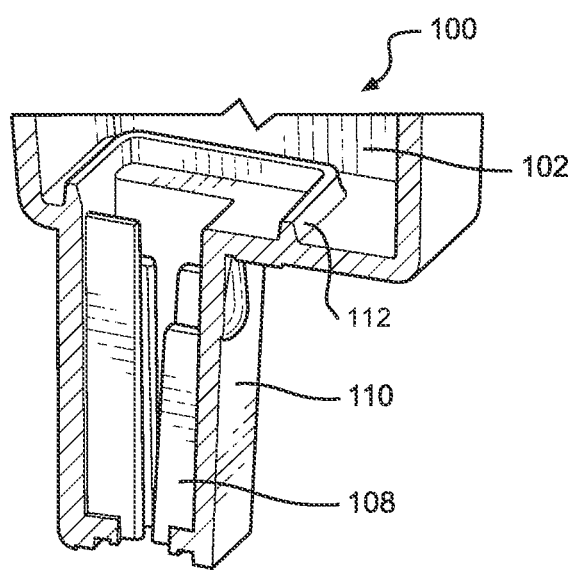
FIG. 10 is a partial side perspective cross-sectional view of a cartridge in a downward orientation according to a second embodiment of the present invention.
Figure 11:
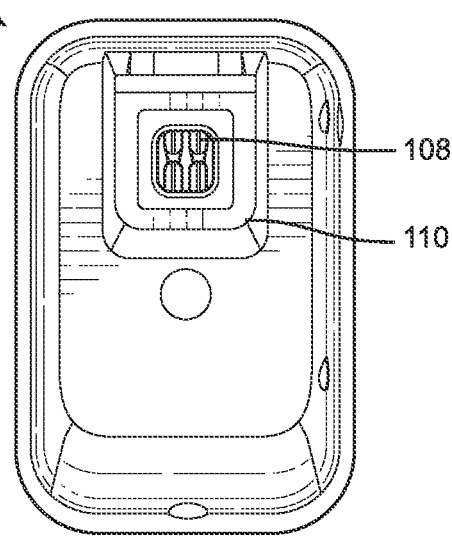
FIG. 11 is a bottom plan view of the exterior of a cartridge according to a second embodiment of the present invention.

With reference now to FIG. 8, there is depicted a top perspective view of the interior of a cartridge 100 according to a second embodiment of the present invention. In this embodiment, there is a different orientation of the ribs 108. For example, this second embodiment still has four ribs 108, but they are disposed parallel to each other, instead of in the cross pattern of the first embodiment. FIGS. 9, 10, and 11 provide different views of this second embodiment, so that it can be better understood.

It is thus appreciated that the invention is not limited to a specific number of ribs 108, a specific orientation of the ribs 108, or a specific combination of the heights of the ribs 108. Further, the ribs 108 are not confined to either a crossed or parallel orientation with respect to one another, but in some embodiments have unequal angles between them, from one rib 108 to another.

Figure 12:
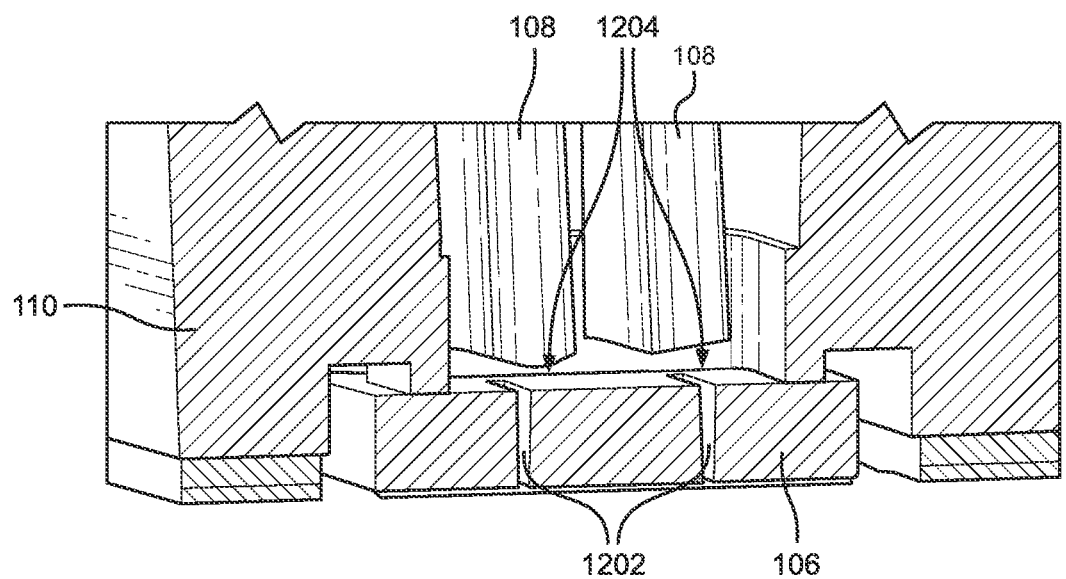
FIG. 12 is a partial side perspective cross-sectional view of a cartridge and a jetting head in a downward orientation according to a second embodiment of the present invention.

With reference now to FIG. 12, there is depicted an expanded partial side perspective cross-sectional view of a cartridge 100, including the tower 110, two ribs 108, and the chip layer of a jetting head 106, all in a downward orientation according to the second embodiment of the present invention. In the embodiment depicted in this view, the distal ends of the ribs 108 form a gap 1204 above the vias 1202 in the chip 106. In some embodiments, the gap 1204 is from about three hundred microns to about five hundred microns in size. Thus, the ribs 108 allow the fluid to be expressed to flow through the gap 1204 and into the vias 1202 and, in this manner, do not interfere with the flow of the fluid from the tower 110 into the jetting head 106.

With reference now to FIG. 12, there is depicted a partial cross-sectional view of the distal end of the tower 110, at the point of attachment of the tower 110 to the chip 106, similar to that as depicted near the bottom of FIG. 1. In this enlarged view, it is easier to see the relationship between the ends of the ribs 108 proximate the surface of the chip 106, and the vias 1202 that are formed in the chip 106.

As depicted in FIG. 12, the ribs 108 have ends proximate the surface of the chip 106, which ends in some embodiments are not flat and parallel to the surface of the heater chip 106 over which they lie. In the embodiment depicted in FIG. 12, the end of the rib 108 on the left-hand side is somewhat pointed or rounded, such that the center portion of the rib 108 that directly overlies the left-hand via 1202 is a bit closer to the surface of the chip 106 than the two sides of the end of the left-hand rib 108. In other embodiments, the end of the rib 108 on the right-hand side of FIG. 12 is slanted such that one side of the end of the rib 108 is farther away from the surface of the chip 106 than the other side. In this manner, any gas bubble 104a or 104b that might attain a position as the end of the rib 108 while in the jetting orientation (upward), would tend to roll off the end of the rib 108 while in the maintenance orientation (downward).

In some embodiments, the ends of the ribs 108 are disposed parallel to and partially overlying the vias 1202. In this manner, the gas bubbles 104a and 104b that are displaced by the ribs 108 tend to not find their way into the vias 1202, where they could be aspirated through the jetting head 106.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A cartridge for jetting a fluid, the cartridge comprising:
   a reservoir for holding and providing the fluid,
   a tower having an interior chamber for receiving the fluid from the reservoir and further providing the fluid, the tower comprising,
      a first end proximate the reservoir,
      a second end distal the reservoir,
      a port in the second end of the tower,
      an interior for conducting the fluid from the reservoir,
      a first rib and a second rib extending along a length of the tower between the first and second ends of the tower, and in the interior of the tower,
      both the first rib and the second rib having second ends that are substantially adjacent the second end of the tower, and
      the first rib has a first end that extends along the length of the tower toward the first end of the tower further than a first end of the second rib, and
   a jetting head having a first via for receiving the fluid from the port, and for expressing the fluid from the cartridge, wherein at least one of the first rib and the second rib at least partially overlaps the first via within the port, and is spaced apart from the first via by a gap.

2. The cartridge of claim 1, wherein the second ends of the first and second ribs are not parallel to a receiving surface of the jetting head in which the first via is formed.

3. The cartridge of claim 1, wherein the tower further comprises a third rib that extends to a different distance than either the first rib or the second rib along the length of the tower.

4. The cartridge of claim 1, wherein the gap is from about three hundred microns to about five hundred microns.

5. The cartridge of claim 1, further comprising a second via in the jetting head, and the first rib at least partially overlaps the first via and the second rib at least partially overlaps the second via.

6. The cartridge of claim 1, wherein the cartridge is a nasal drug delivery cartridge.

7. The cartridge of claim 1, wherein the ribs tend to prohibit gas bubbles from aspirating into the first via when the cartridge is oriented with the tower above the reservoir.

8. The cartridge of claim 1, wherein the first via and the second ends of both the first and second ribs are oriented substantially parallel one to another.

9. The cartridge of claim 1, wherein the first via and the second ends of both the first and second ribs are oriented substantially perpendicularly one to another.

10. A cartridge for jetting a fluid, the cartridge comprising:
    a reservoir for holding and providing the fluid,
    a tower having an interior chamber for receiving the fluid from the reservoir and further providing the fluid, the tower comprising,
       a first end proximate the reservoir,
       a second end distal the reservoir,
       a port in the second end of the tower,
       an interior for conducting the fluid from the reservoir,
       at least a first rib and a second rib extending along a length of the tower between the first and second ends of the tower, and in the interior of the tower,
       both the first rib and the second rib having second ends that are substantially adjacent the second end of the tower, and
       the first rib extending further than the second rib along the length of the tower toward the first end of the tower, and
    a jetting head having at least a first via for receiving the fluid from the port, and for expressing the fluid from the cartridge,
    wherein,
       both the first rib and the second rib at least partially overlap the first via within the port, and are spaced apart from the first via by a gap.

11. The cartridge of claim 10, wherein the second ends of the first and second ribs are not parallel to a receiving surface of the jetting head in which the first via is formed.

12. The cartridge of claim 10, wherein the gap is from about three hundred microns to about five hundred microns.

13. The cartridge of claim 10, further comprising a second via in the jetting head, and both a third rib and a fourth rib that at least partially overlap the second via, wherein the first rib, second rib, third rib, and fourth rib all extend to different lengths within the tower.

14. The cartridge of claim 10, wherein the cartridge is a nasal drug delivery cartridge.

15. The cartridge of claim 10, wherein the ribs tend to prohibit gas bubbles from aspirating into the first via when the cartridge is oriented with the tower above the reservoir.

16. A cartridge for jetting a fluid, the cartridge comprising:
- a reservoir for holding and providing the fluid,
- a tower having an interior chamber for receiving the fluid from the reservoir and further providing the fluid, the tower comprising,
  - a first end proximate the reservoir,
  - a second end distal the reservoir,
  - a port in the second end of the tower,
  - an interior for conducting the fluid from the reservoir,
  - at least a first rib and a second rib extending along a length of the tower between the first and second ends of the tower, and in the interior of the tower,
  - both the first rib and the second rib having second ends that are substantially adjacent the second end of the tower, and
  - the first rib extending further than the second rib along the length of the tower toward the first end of the tower, and
- a jetting head having at least a first via for receiving the fluid from the port, and for expressing the fluid from the cartridge, wherein,
- both the first rib and the second rib at least partially overlap the first via within the port, and are spaced apart from the first via by a gap,
- the second ends of the first and second ribs are not parallel to a receiving surface of the jetting head in which the first via is formed, and
- the gap is from about three hundred microns to about five hundred microns.

17. The cartridge of claim 16, further comprising a second via in the jetting head, and both a third rib and a fourth rib at least partially overlap the second via, wherein the first rib, second rib, third rib, and fourth rib all extend to different lengths within the tower.

18. The cartridge of claim 16, wherein the cartridge is a nasal drug delivery cartridge.

19. The cartridge of claim 16, wherein the first and second ribs tend to prohibit gas bubbles from aspirating into the first via when the cartridge is oriented with the tower above the reservoir.

20. The cartridge of claim 16, wherein the first via and the second ends of both the first and second ribs are oriented substantially parallel one to another.

* * * * *